United States Patent [19]

Paradis

[11] 4,448,684
[45] May 15, 1984

[54] SOLVENT PRESSURIZATION SYSTEM
[75] Inventor: Roland C. Paradis, Newtown, Conn.
[73] Assignee: The Perkin-Elmer Corporation, Norwalk, Conn.
[21] Appl. No.: 461,789
[22] Filed: Jan. 28, 1983
[51] Int. Cl.³ .............................................. B01D 15/08
[52] U.S. Cl. .................................... 210/198.2; 55/386
[58] Field of Search ...................... 210/198.2, 656, 659; 55/53, 67, 386

[56] References Cited

U.S. PATENT DOCUMENTS

| | | | |
|---|---|---|---|
| 3,934,456 | 1/1976 | Munk | 210/198.2 |
| 4,116,046 | 9/1978 | Stein | 210/198.2 |
| 4,133,767 | 1/1979 | Bakalvar et al. | 210/659 |
| 4,165,284 | 8/1979 | Guillemin et al. | 210/198.2 |
| 4,374,656 | 2/1983 | Schrenker et al. | 55/386 N |

OTHER PUBLICATIONS

Rainin Instrument Co. Catalog, p. 52, Rainin Inst. Co., Woburn, Ma.

*Primary Examiner*—John Adee
*Attorney, Agent, or Firm*—F. L. Masselle; E. T. Grimes; R. A. Hays

[57] ABSTRACT

A solvent pressurization system includes a depressurization means which operates to change the operating mode for pressurized solvent delivery to a sparging mode when the access door of the solvent compartment is opened. Consequently, an operator is protected from accidental exposure to pressurized solvent vessels.

15 Claims, 3 Drawing Figures

SOLVENT PRESSURIZATION SYSTEM

BACKGROUND OF THE INVENTION

The present invention generally relates to a system for pressurizing a plurality of vessels and, in particular, relates to a system for pressurizing a plurality of solvent vessels in a liquid chromatographic instrument.

In recent years liquid chromatography systems have evolved such that unattended analysis involves separating a particular sample a number of times but using a different solvent composition, or mixture each time. Alternately, a variety of different samples can be analyzed, each with a different solvent composition. In such systems, in order to enhance the flow of individual solvent components, it is helpful to individually pressurize each solvent container. Thus, when that solvent component is required by the liquid chromatography system the solvent readily flows from the container due to the pressure thereon rather than being flow regulated by a suction created in a piston cylinder. A major advantage to pressurizing the solvent components is that air bubbles, usually found in nonpressurized systems, are eliminated. Consequently, since air bubbles tend to reduce the performance of the solvent pump, the entire liquid flow exhibits an increased efficiency. However, since many solvents are acids or other hazardous materials and since any liquid under pressure is potentially injurious to both equipment and personnel, a number of potential dangers exist in present liquid chromatography solvent gradient systems.

One potential danger exists in the accessibility of the solvents, in particular, when those solvents are pressurized. The conventional approach to avoiding this danger is to provide a simple interlock which locks the access door to the solvent compartment whenever any solvent is pressurized. Unfortunately, most simple interlocks can be simply bypassed or manually overridden.

Another danger exists from system leakage. Leakage of solvent material or the leakage of external air into the system can have serious consequences. For example, the leakage of solvent material, such as an acid, from the system to, say, the laboratory workbench presents a danger to both personnel and equipment. Another consequence of leakage, perhaps of lesser danger to personnel but nevertheless serious, is unequal pressurization among the various solvent containers. Unequal pressurization among the solvent containers generally results in misproportioning of the solvent components in the resultant solvent mixture.

Yet another common problem occurs during sparging, i.e., the degassing of a solvent component by passing helium therethrough. In conventional systems the solvent container, or bottle, is purchased with a valve as a single unit. Hence, each bottle has a valve associated therewith. During sparging it is not uncommon for solvent material to be forced back across the valve and into the system pump. This can seriously impair the accuracy of subsequent measurements since the actual solvent mixture becomes inaccurate and unknown.

In consideration of the above, it is highly desirable to provide a solvent pressurization system which substantially, if not completely, alleviates these dangers.

SUMMARY OF THE INVENTION

Accordingly, it is one object of the present invention to provide a solvent pressurization system which is both safe and efficient.

This object is accomplished, at least in part, by a solvent pressurization system having a plurality of sealed solvent vessels including means for providing substantially equal pressure to each from a single pressurized gas source. It is preferred that such a system further include a means for relieving that pressure from the vessels when the access door thereto is opened.

Other objects and advantages will become apparent to those skilled in the art from a reading of the following detailed specification in light of the attached drawing and the claims appended hereto.

BRIEF DESCRIPTION OF THE DRAWING

The drawing, not drawn to scale, attached hereto includes.

DETAILED DESCRIPTION OF THE INVENTION

Figure 1:
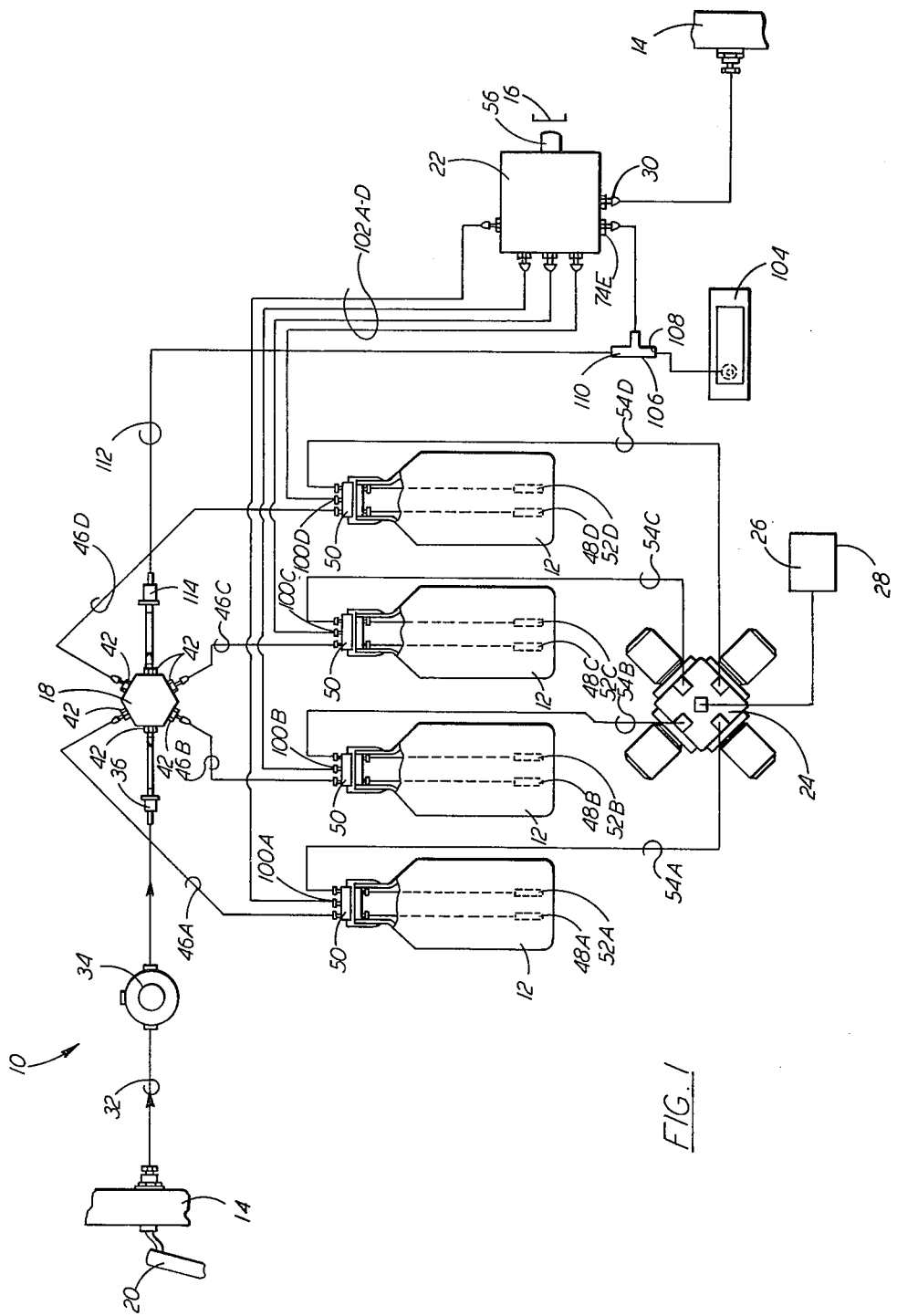
FIG. 1, which is a schematic block diagram of a solvent pressurization system embodying the principles of the present invention.

A solvent pressurization system, generally indicated at 10 in FIG. 1, embodying the principles of the present invention includes a plurality of solvent vessels 12 within a closable compartment 14 having an access door 16. The system 10 also includes a means 18 for substantially equally distributing gaseous pressure among the solvent vessels 12. In the preferred embodiment the solvent vessels 12 are pressurized from a single source 20 of gas, for instance, helium. Further, the system 10 is provided with a means 22 for depressurizing the solvent vessels 12 when the integrity of the compartment 14 is breeched by opening the access door 16.

The system 10 has two primary operating modes. During one operating mode the solvent vessels 12 are pressurized and solvent is delivered via a multi-port proportioning valve 24 to the cylinder 26 of a chromatographic pump 28. This mode is hereinafter referred to as the delivery mode. During the other operating mode gas is passed through the solvents for the purpose of removing air bubbles therefrom, i.e., commonly known as degassing or sparging. After passing through the solvents the gas is directed to a vent port 30 which is usually connected to a ventilation hood (not shown). This mode is hereinafter referred to as the sparging mode.

In both the delivery and sparging modes, pressurized gas flows, preferably at about 35.5 KPa (5 p.s.i.), from the gas source 20 through one conduit 32 via a gas pressure regulator 34 to the distribution means 18. Preferably a conventional unidirectional flow check valve 36 is positioned in the conduit 32 between the regulator 34 and the distribution means 18. The inclusion of check valve 36 ensures that solvent material can not, if, for example, gas pressure is reduced for any reason, flow back through the regulator 34 and vent to the ambient. Thus, the creation of hazardous fumes around the instrument and work area is avoided. A more detailed view of the preferred distribution means 18 is shown in FIG. 2.

Figure 2:
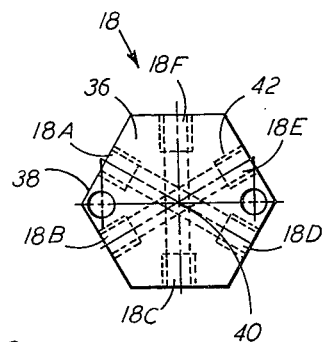
FIG. 2, which is a detailed view of the solvent distribution block shown in FIG. 1.

As shown in FIG. 2, the distribution means 18 includes a machined block 36 of, for example, brass, and includes six bores, 18A-18F, each of which extends from the periphery 38 to a common internally centered cavity 40. In this example, the bores, 18A-18F, have diameters of about 0.4 centimeters. Preferably, although not necessarily, for machining convenience, the periphery 38 of the block 36 is in the shape of a regular hexagon having six equal flat sides about 1.8 centimeters long. The block 36 can be fabricated by conventional machining techniques. The external portion 42 of each bore 18A-18F is fitted with a conduit connection means 44 (shown in FIG. 1). The means 44 can be any known gas connector fitting compatible with the gas conduits used in the system 10.

For the purpose of this discussion, port 18A is designated as the port connected to the conduit 32 for conducting pressurized gas from the source 20 to the common cavity 40 within the block 36. As the cavity 40 is a common connecting point for all six bores, 18A-18F, the pressurized gas entering the cavity 40 is equally distributed to the remaining five ports, 18B-18F, of the block 36.

The pressurized gas is distributed, equally in pressure, to ports 18B, 18C, 18D and 18E, which are connected via conduits 46A, 46B, 46C and 46D, to respective solvent filters 48A, 48B, 48C, 48D within respective solvent vessels 12. The use and purpose of the sixth port 18F is more fully discussed below. It is sufficient to point out here that the gas conduit connected thereto includes an in-line unidirectional check valve which operates to close port 18F from pressure flow thereacross from the cavity 40.

The connection from conduits 46A-D to filters 48A-D within the solvent vessels 12 is preferably made via a sealed cap 50 affixed to each vessel 12. The solvent vessels 12 and associated caps 50 are well known in the field of liquid chromatography. Preferably, the solvent vessels 12 are at least one liter in volume. Conventionally, these units are adapted to include individual valves between the pressure source and the vessel 12, the need for which individual valves has been obviated by the design of the present system 10. Nevertheless, it is desirable to point out that each vessel 12 and cap 50 unit includes three connections to the cap 50, two of which extend into the vessel 12 and terminate therein with filters, e.g., filters 48A-D and 52A-D, respectively. Henceforth conduits 46A-D are referred to as vessel pressure inputs.

Upon being pressurized, in the delivery mode, solvent is forced through the filters 52A-D and from the vessels 12.

Thus, solvent is delivered to the conventional multiport proportioning valve 24 from the vessels 12 via output conduits 54A-D. For reasons more fully discussed hereinafter, solvent is prevented, in the delivery mode, from exiting the vessel 12 via the third connection to the cap 50.

Figure 3:
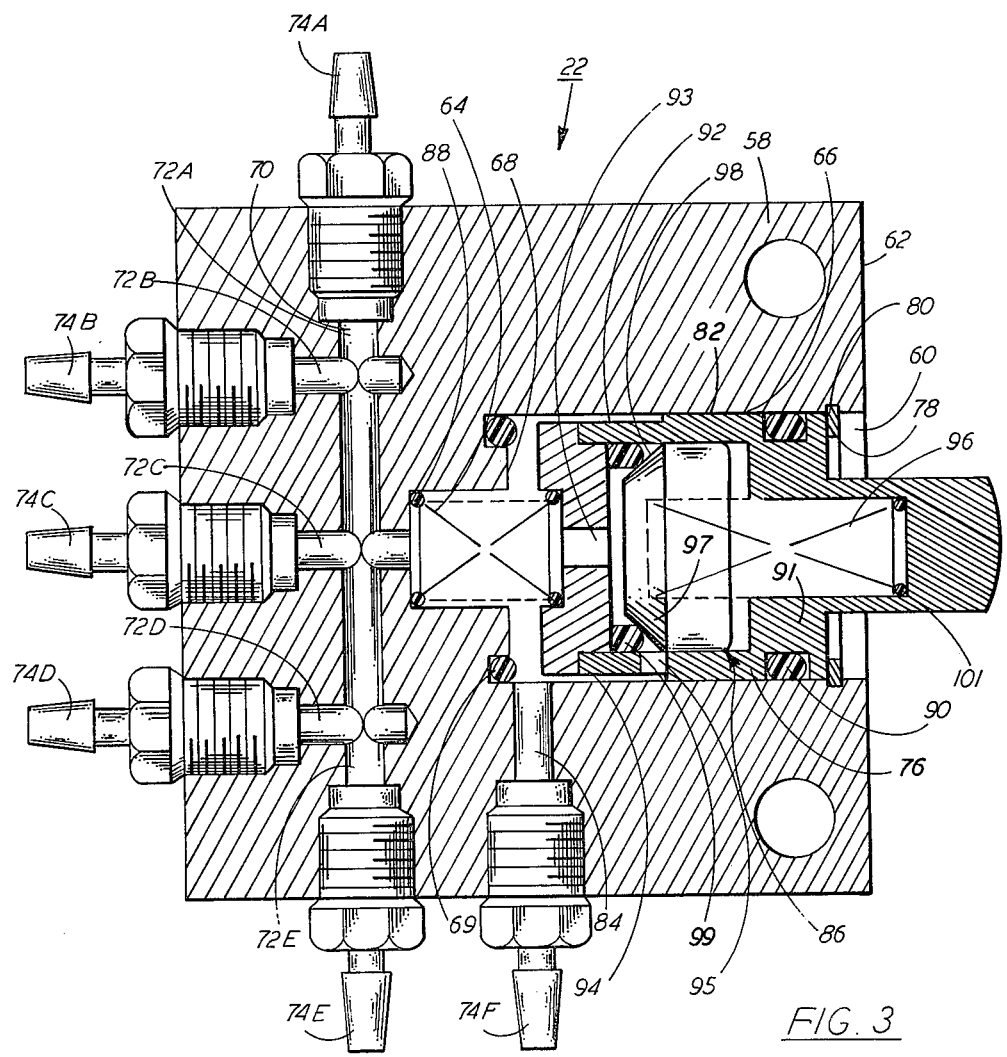
FIG. 3, which is a detailed view of the pressure safety mechanism.

The above-described pressurized delivery of solvent to the multiport valve 24 can only occur when the access door 16 is closed and acting to depress a plunger 56 on the depressurizing means 22. A detailed view of the pressurizing means 22 is presented in FIG. 3. As shown therein the means 22 includes a body 58 fabricated from, for example, brass. Brass is preferred as the material for the body 58, the block 36 and all conventional gas conduit fittings by reason of its ease of machining and its ability to be electroplated. The body 58 includes an opening 60 extending from one surface 62 thereof into the body 58. The opening 60 has a comparatively smaller portion 64 and a comparatively larger portion 66, a shoulder 68 being formed at the interface thereof. The shoulder 68 is adapted to accept an O-ring 69, against which a gaseous seal can be formed with piston 76, more fully discussed hereinafter. The smaller portion 64 terminates in gaseous communication with a common bore 70. The body 58 further includes at least five openings 72A-E also in gaseous communication with the common bore 70. The openings 72A-E are adapted to connect to gas conduits via fittings 74A-E, preferably conventional nickel-plated brass fittings, at the respective surface terminations thereof.

A piston 76 is slidably positioned within the larger portion 66 and retained therein by a retaining ring 78 inserted in a peripheral groove 80 extending into the wall 82 of the larger portion 66 which groove 80 is slightly recessed from the surface 62 of the body 58. A venting port 84 extends from the wall 82 of the larger portion 66 to a surface 86 of the body 58 and is provided with a fitting 74F thereat. The port 84 is so located that it is in gaseous communication with the common bore 70, via the smaller portion 64 when the piston 76 is distal the smaller portion 64 and isolated from the common bore 70 when the piston 76 is proximate the smaller portion 64. To ensure sufficiently rapid movement, the need for which will be discussed hereinafter, the means 22 includes a compression spring 88 located within the smaller portion 64 and secured to the piston 76 in a conventional manner. Thus, when the plunger 56 is pushed toward the smaller portion 64, such as by closing the access door 16, the spring 88 is compressed. When the door 16 is opened the force of the spring 88 forces the piston 76 toward, and preferably against, the retaining ring 78 whereby venting occurs. A piston ring 90 is provided to prevent gas leakage across the piston 76.

While the above-described piston 76 is fully acceptable and functional it is preferred, as an additional system safety function, that an over pressure relief valve means providing a pressure venting function be provided. Such a feature is preferably implemented by a piston 76 which includes a first segment 91 and a second segment 92 which second segment 92 includes an opening 93 therethrough. The first and second segments, 91 and 92 respectively, being maintained in abutting relationship by the spring 88. As shown, the second segment 92 abuts the first segment 91 at a shoulder thereof. The first segment 91 includes a section 94, proximate the second segment 92, having a reduced outside diameter and a vent 95 through the wall of section 94. Further, the first segment 91 includes a chamber 96 therein within which a second piston 97 is slidably mounted. Preferably, the second piston 97 has a beveled face 98 and abuts against an O-ring 99 to seal the chamber 96 when the beveled face 98 is proximate the second segment 92 of the piston 76. In this embodiment, the second piston 97 is spring loaded, via spring 101, against the O-ring 99 under normal operating pressure. However, if excess pressure, i.e., pressure beyond a preselected level, for example, 71 KPa (10 p.s.i.), is reached that pressure is transferred to the beveled face 98 via opening 93. The excess pressure acts against the spring 101 to move the second piston 97 off the O-ring 99 and permit gaseous communication between the opening 93 and the vent 95. The vent 95 nevertheless is, because of the reduced diameter of the section 94, in gaseous communication with the vent port 84 even when the access door 16 is closed. Thus, if the system 10 is over pressured, for whatever reason, that excess pressure is safely vented via the vent port 84.

In the preferred embodiment, the smaller portion 64 has a diameter of about 0.84 cm (0.37 inch) and the larger portion 66 has a diameter of about 2.39 cm (0.864 inch). The piston 76 has an outside diameter of about 2.29 cm (0.861 inch) with the section 94 having a diameter of about 2.03 cm (0.8 inch). Thus, there is a radial space of about 0.81 cm (0.32 inch) between the section 94 and the wall of the large portion 66. The spring 101 is chosen such that it is compressed when a pressure of about 71 KPa (10 p.s.i.) is applied to the beveled face 98 of the piston 97. The spring 88 is chosen such that it moves the piston 76 toward the retaining ring 78 with ease, i.e., it overcomes the frictional force between the O-ring 90 and the wall 82 when the access door 16 is opened. It is preferred that the chamber 96 within the piston 76 have a diameter of about 1.74 cm (0.687 inch). The depressurizing means 22 can be fabricated using well known machining techniques. The conduits and fittings used throughout the system 10 are equally well known in the art.

As previously mentioned, solvent is prevented, in the delivery mode, from exiting the vessels 12 via the third connections to the caps 50. As shown in FIG. 1, the third connections 100A–D are in gaseous communication with the depressurized means 22 via the conduits 102A–D, which conduits 102A–D connect to fittings 74A–D respectively. Thus, with the access door 16 closed and consequently the venting port 84 sealed from the common bore 70, gas flow from the vessels 12 via the third connections 100A–D, under normal operating conditions, is prevented. Since gas flow from the vessels 12 is blocked, the gas pressure rises within the vessels 12 to force solvent therefrom via filters 52A–D, through output conduits 54A–D respectively.

However, under abnormal operating conditions, if the pressure within the vessels 12 becomes excessive the spring 101 will compress to allow the second piston 97 to slide toward the plunger 56 and uncover, or open, the vent 95 and thus communicate with the venting port 84. Upon the opening of the venting port 84 the vessels 12, via the conduits 102A–D through the common bore 70 are in gaseous communication therewith and the excess pressure within the vessels 12 is relieved.

As previously mentioned, the sparging mode can only be achieved when the access door 16 is open and the venting port 84 is in gaseous communication with the common bore 70. In this condition, the system 10 supplies helium gas from the source 20 to the vessels 12 via the conduits 46A–D. The gas bubbles through the solvent and, since the multi-port valve 24 is closed, exits through the third connections 50A–D where it is conducted to the venting port 84.

Thus, if the system 10 is operating in the delivery mode and the access door 16 is, for whatever reason, opened, the system 10 instantly, and inherently, switches to the sparging mode. In this manner, there is never a danger of an operator accidentally becoming exposed to the solvent vessels 12 when they are under pressure.

As with most systems, it is highly desirable to monitor and/or ascertain the instantaneous pressure status of the system 10. In the preferred embodiment, this is accomplished by connecting a conventional pressure gauge 104 to the fitting 74E of the common bore 70. Preferably the fitting 74E of the common bore 70 is connected to a "TEE"-junction 106 one end 108 of which is in gaseous communication with the pressure gauge 104. The other end 110 of the "TEE"-junction 106 is returned to the sixth port 18F of the gas distribution means 18 by gas conduit 112. As previously discussed, gas conduit 112 includes an in-line, unidirectional check valve 114 which operates to equilibrate pressure between the cavity 40 of the block 18 and the gas pressure in the vessel 12 above the solvent. For example, if after sparging the solvent in one particular vessel 12, by warming, creates an increased pressure in the space above the solvent, the solvent material, in conventional systems has a tendency to back up the input conduit 46A. Such a condition contaminates the gas conduits and can result in the uncontrolled mixing of solvent. Under the above conditions, the excess, or differential, pressure in any vessel 12 is returned to the common bore 70 for equal distribution to all of the vessels 12. Thus, the pressurization among the vessels 12 is equilibrated and solvent does not back up the input conduits 46A–D. However, if the equal pressures in the vessels 12 exceeds a preselected value, for example, about 0.7 KPa (0.1 p.s.i.), the check valve 114 opens to equilibrate the pressure in cavity 40 with that of the vessels 12.

From the above description it will be understood that the system 10 has many advantages over conventional solvent pressurization systems, not the least of which is the safety features as described.

While the description herein has been directed to a single preferred system embodiment, other advantages and arrangements are conceivable which do not depart from the scope of this invention. Consequently, the embodiments described herein are deemed exemplary of and not as limiting to, the invention which is limited only by the appended claims and the reasonable interpretation thereof.

What is claimed is:

1. A solvent pressurization system for use in liquid chromatography; said system comprising:
   a source of pressurized gas;
   a plurality of sealed vessels, said vessels being adapted to hold solvents therein; each said vessel having a gas input port, said vessels being located within a closable cabinet;
   means for simultaneously communicating said pressurized gas from said gas source to each one of said plurality of sealed vessels such that the pressure within each said vessel is substantially equal to the pressure within every other said vessel;
   means for regulating the pressure to said vessels;
   means for relieving said pressure from said vessels when said cabinet is opened;
   means for depressurizing said vessels when said pressure within said vessels exceeds a preselected venting pressure; and
   means for equilibrating the pressurized gas when said pressure exceeds the regulated pressure but remains less than said preselected venting pressure.

2. System as claimed in claim 1 wherein said gas simultaneous communicating means includes:
   a body being an internal cavity; and
   a plurality of bores extending from the periphery of said body to said cavity, said cavity being in common gaseous communication with all of said plurality of bores whereby when pressurized gas communicates with said cavity the pressure of said gas is substantially equal at each said bore.

3. System as claimed in claim 2 wherein:
said source of pressurized gas gaseously communicates with one of said plurality of bores via an in-line unidirectional check valve.

4. System as claimed in claim 1 wherein said pressure relief means includes:
a biassed first piston within a first piston chamber, said first piston chamber having a vent port through one wall thereof, said port being sealable by said piston;
a plunger protruding from and in rigid contact with said first piston, said plunger extending away from said piston such that upon depressing said plunger said biassed piston is moved so as to seal said vent port, said plunger being cooperatively arranged so as to be depressed by said access door upon closure thereof.

5. System as claimed in claim 1 further comprising:
means for depressurizing said vessels when said pressure within said vessels exceeds a preselected venting pressure.

6. System as claimed in claim 5 wherein said means for depressurizing said vessels comprises:
a common bore in gaseous communication with said vessels;
a second piston within a second piston chamber, said second piston being biassed against a chamber opening, said opening being in gaseous communication with said common bore;
a venting opening through the wall of said second chamber, said venting opening being sealed when said second piston is biassed against said second chamber opening and being unsealed when the pressure exceeds said preselected venting pressure whereby gas vents via said venting opening and said system depressurizes.

7. System as claimed in claim 6 wherein:
said second piston chamber is located within said pressure relieving means.

8. System as claimed in claim 5 further comprising:
means for regulating the pressure to said vessels; and
means for equilibrating the pressurized gas when said pressure exceeds the regulated pressure but remains less than said preselected venting pressure.

9. System as claimed in claim 1 wherein said equilibrating means includes:
a common bore in gaseous communication with said vessels;
a return gas conduit forming gaseous communication between said common bore and said means for simultaneous communication means; and
an in-line unidirectional check valve in said return gas conduit and operative to allow gaseous communication from said common bore to said simultaneous communication means only at pressures exceeding said regulated pressure.

10. System as claimed in claim 1 further comprising:
means for degassing said solvents within said solvent vessels.

11. System as claimed in claim 1 further comprising:
means for regulating the pressure to said vessels; and
means for equilibrating the pressurized gas when said pressure exceeds the regulated pressure but is less than said preselected venting pressure.

12. System as claimed in claim 1 further comprising:
means for degassing said solvents within said solvent vessels.

13. A solvent pressurization system for use in liquid chromatography, said system comprising:
a source of pressurized gas;
a plurality of sealed vessels, said vessels being adapted to hold solvents therein; each said vessel having a gas input port, said vessels being located within a closable cabinet;
means for simultaneously communicating said pressurized gas from said gas source to each one of said plurality of sealed vessels such that the pressure within each said vessel is substantially equal to the pressure within every other said vessel;
means for relieving said pressure from said vessels when said cabinet is opened; and
means for depressurizing said vessels when said pressure within said vessels exceeds a preselected venting pressure said depressurizing means including a common bore in gaseous communication with said vessels said means further including a piston within a piston chamber, said piston being biassed against a chamber opening, said opening being in gaseous communication with said common bore; a venting opening through the wall of said chamber, said venting opening being sealed when said piston is biassed against said chamber opening and being unsealed when the pressure exceeds said preselected venting pressure whereby gas vents via said venting opening and said system depressurizes.

14. System as claimed in claim 13 wherein:
said piston chamber is located within said pressure relieving means.

15. A solvent pressurization system for use in liquid chromatography, said system comprising:
a source of pressurized gas;
a plurality of sealed vessels, said vessels being adapted to hold solvents therein; each said vessel having a gas input port, said vessels being located within a closable cabinet;
means for simultaneously communicating said pressurized gas from said gas source to each one of said plurality of sealed vessels such that the pressure within each said vessel is substantially equal to the pressure within every other said vessel; and
means for relieving said pressure from said vessels when said cabinet is opened said pressure relieving means including a biassed piston within a piston chamber, said piston chamber having a vent port through one wall thereof, said port being sealable by said piston, said piston having a plunger protruding therefrom and in rigid contact therewith, said plunger extending away from said piston such that upon depressing said plunger said biassed piston is moved so as to seal said vent port, said plunger being cooperatively arranged so as to be depressed by said access door upon closure thereof.

* * * * *